United States Patent
Hsi et al.

(10) Patent No.: US 6,749,623 B1
(45) Date of Patent: Jun. 15, 2004

(54) METHOD AND APPARATUS FOR CATHETER PHOTOTHERAPY WITH DOSE SENSING

(76) Inventors: Richard A Hsi, 1415 2$^{nd}$ Ave. #1109, Seattle, WA (US) 98101; Arye Rosen, 508 Heartwood Rd., Cherry Hill, NJ (US) 08003-3220; Carmen E Rodriguez, 13 Dover Dr., Lindenwold, NJ (US) 08021

( * ) Notice: Subject to any disclaimer, the term of this patent is extended or adjusted under 35 U.S.C. 154(b) by 53 days.

(21) Appl. No.: 09/591,947

(22) Filed: Jun. 12, 2000

Related U.S. Application Data
(60) Provisional application No. 60/193,928, filed on Mar. 31, 2000.

(51) Int. Cl.$^7$ .................................................. A61K 5/00
(52) U.S. Cl. ....................................................... 607/88
(58) Field of Search ................................ 606/7, 14–15; 604/96, 101; 607/88, 89

(56) References Cited

U.S. PATENT DOCUMENTS

| | | | | |
|---|---|---|---|---|
| 4,967,745 A | * | 11/1990 | Hayes et al. .................. 606/14 |
| 5,350,375 A | * | 9/1994 | Deckelbaum et al. ....... 128/898 |
| 5,562,100 A | * | 10/1996 | Kittrell et al. .............. 128/665 |
| 5,797,868 A | * | 8/1998 | Leone .......................... 604/21 |
| 5,989,245 A | * | 11/1999 | Prescott ....................... 606/14 |
| 6,013,053 A | * | 1/2000 | Bower et al. ................. 604/96 |
| 6,030,411 A | * | 2/2000 | Lawandy ...................... 607/88 |
| 6,096,030 A | * | 8/2000 | Ortiz ............................ 606/14 |
| 6,159,236 A | * | 12/2000 | Biel ............................. 607/92 |
| 6,162,242 A | * | 12/2000 | Peyman ....................... 607/88 |

* cited by examiner

Primary Examiner—Michael Peffley
Assistant Examiner—Peter Vrettakos
(74) Attorney, Agent, or Firm—Duane Morris LLP

(57) ABSTRACT

A photodynamic therapy method administers, to a patient to be treated, a photosensitive medication which fluoresces when illuminated. The fluorescent light is an indication of the instantaneous phototherapy dose. A catheter according to the invention includes a probe or sensor arrangement for generating a signal representing the instantaneous amplitude of the fluorescence or the incident illumination. The signal is integrated to produce a signal representing the total dose of phototherapy. The photodynamic therapy is terminated when the integrated signal indicates a particular value. The catheter in one embodiment includes an array of semiconductor light sources near its distal end, energized from the proximal end. In another embodiment, the light source is external to the patient, and the light is conducted to the distal end of the catheter by one or more optical fibers. The light sensor may be an optical fiber extending from the proximal to the distal end of the catheter, with a probe end which is directive or omnidirectional. In this case, the dose signal is detected by a photodiode exterior to the catheter and the detected signal is integrated to generate a signal indicative of cumulative dose. In another embodiment, the photodiode is located near the distal end of the catheter.

14 Claims, 11 Drawing Sheets

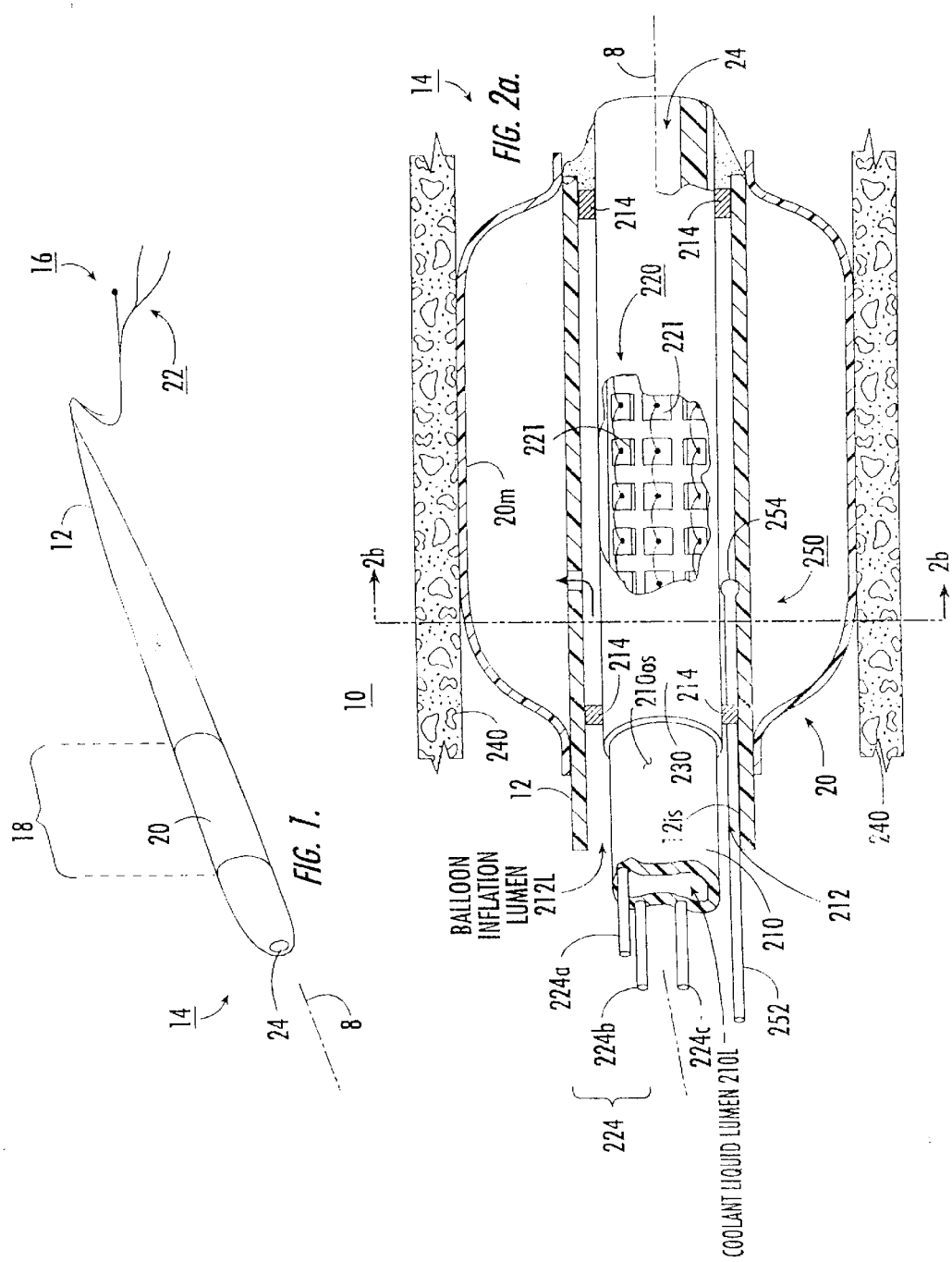

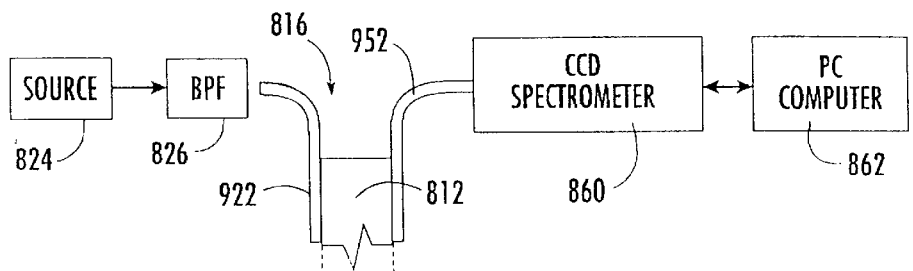
FIG. 9a.
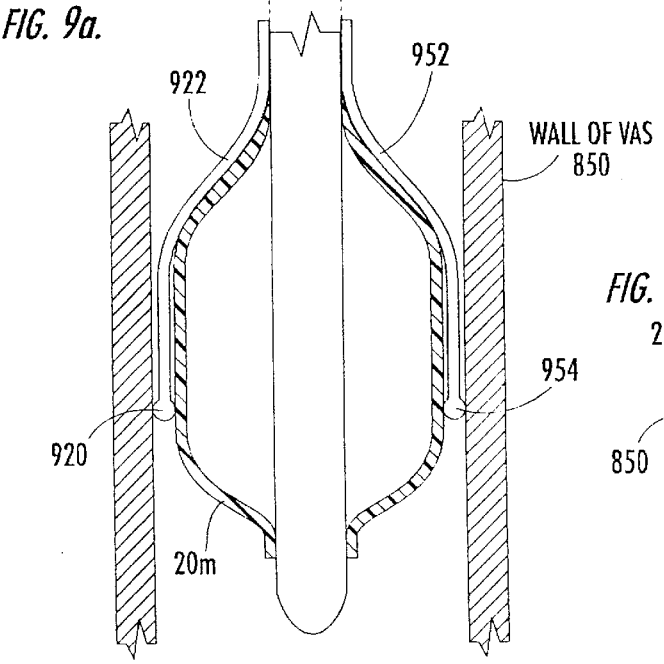
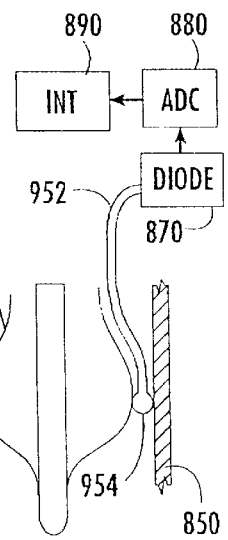
FIG. 9d.
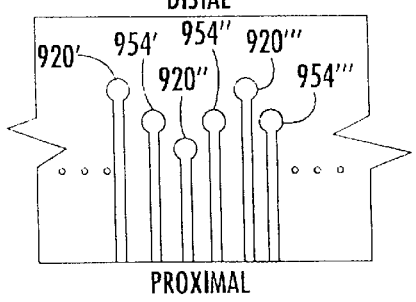
FIG. 9c.
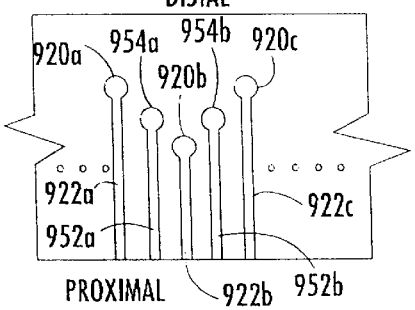
FIG. 9b.

METHOD AND APPARATUS FOR CATHETER PHOTOTHERAPY WITH DOSE SENSING

This patent application claims priority from Provisional application serial No. 60/193928, filed Mar. 31, 2000.

FIELD OF THE INVENTION

This invention relates to phototherapy, and more particularly to phototherapy by means of a catheter.

BACKGROUND OF THE INVENTION

Photodynamic therapy (PDT) is a treatment modality using light of an appropriate wavelength to activate a photosensitizer in the presence of oxygen, resulting in localized tissue necrosis. The depth of light penetration, and consequently of the tissue necrosis, is a function of light wavelength, and is typically less than one centimeter. This depth limitation characteristic makes PDT an ideal treatment for tissues with superficial lesions.

Barrett's esophagus (BE) is one such lesion which is an ideal target for PDT. It is a lesion of the superficial lining of the esophagus characterized by the replacement of the normal stratified squamous epithelium by a metaplastic columnar epithelium. It is an acquired condition that develops predominantly from chronic gastroesophageal reflux disease (GERD). BE appears endoscopically as finger-like projections or islands of epithelium. Patients with BE are at risk for the development of dysplasia. On a background of dysplastic epithelium, esophageal adenocarcinoma may then develop. Barrett's esophagus with dysplasia, therefore, has been identified as a premalignant condition. The estimated risk for developing adenocarcinoma in patients with this condition has been reported to be from 30 to 169 times greater than that of the general population.

The management of BE with high grade dysplasia is somewhat controversial. Some advocate close observation with regular endoscopy and biopsies until esophageal cancer is found. Unfortunately, treatment after documentation of frank invasive cancer may result in lower cure rates. Some advocate total esophagectomy before cancer is found. There is, however, a substantial morbidity and mortality associated with this type of radical surgery. Therefore, a minimally invasive technique such as PDT should be ideal for lesions such as those of BE. Several studies have reported on the use of PDT for treatment of BE and also of superficial carcinoma. Extensive mucosal ablation was noted with abolishment of high grade dysplasia or superficial carcinoma in the majority of patients.

Improved photodynamic therapy apparatus and methods are desired.

SUMMARY OF THE INVENTION

A remaining problem with treatment of BE by use of photosensitive medications is that the dose of photosensitizer medication at the region of treatment, and the incident light dose (fluence) acting on the region of treatment, are difficult to control.

A phototherapy method according to the invention includes the step of administering a photosensitive medication to a patient, which medication fluoresces in response to light flux. Energy is applied to a proximal end of a catheter adjacent tissue of said patient, to thereby cause light flux from a distal end of said catheter, whereby the light flux causes the photosensitive medication to fluoresce. A signal is generated which is representative of one of (which is to say, is either or both of) the light flux and the fluorescence. The signal so generated, which may be either in the form of a light sample or an electrical signal, is coupled by way of the catheter to a location without (outside of) the patient. The signal may be analyzed to determine any of several parameters.

A phototherapy method according to another aspect of the invention includes the steps of administering a medication to a patient, which medication, when activated by light flux, both leads to tissue necrosis and fluoresces within a specific range of wavelengths in response to light flux. Light flux is applied to a vas (any tube-like anatomical organ, duct, or cavity, including, but not limited to, esophagus, blood vessels, lymphatics, urethra, lung/trachea, cervix, oral cavity, and rectum) of the patient through a catheter (which may be introduced into the vas directly, or by penetration through tissue, such as muscle tissue, as by means of a needle), for thereby performing phototherapy, and causing the medication to fluoresce in response to the flux. At least a portion of the fluorescent light is routed to a location without the patient by means of the catheter. The method includes the further step of establishing, from at least the fluorescence, at least one of (a) the intensity of the applied flux and (b) the duration of the applied flux.

In a particular mode of the method of the invention, the step of determining from at least the fluorescence includes the step of determining at least one of the power and the intensity of the fluorescence. In a particular mode, the step of administering medication includes the step of administering 5-aminolevulinic acid orally. The medication may also be injected or administered topically. According to this particular mode, the step of applying light flux includes the step of applying a light flux having its peak amplitude at a wavelength in the vicinity of $5 (10^{-7})$ meters. This may be accomplished, in one version, by generating white light, and passing the white light through an optical bandpass filter having a peak in transmission response in the vicinity of $5 (10^{-7})$ meters.

In a preferred mode of practicing the method of the invention, the step of applying light flux includes the step of applying electrical excitation to a plurality of semiconductor light sources associated with a distal portion of the catheter, which semiconductor light sources produce light in the vicinity of $5 (10^{-7})$ meters.

The inventive method may also include, before the step of administering medication, the sensing of the fluorescence of the vas of the patient in response to a flux of light.

According to another aspect of the invention, a catheter for phototherapy comprises an elongated body defining an axis of elongation, a distal region, and a proximal region, which distal region is adapted for introduction into a vas of a patient. An elongated array of semiconductor light sources is associated with the catheter body near the distal region. The semiconductor light sources and the body near the semiconductor light sources are such that, when the light source(s) are energized, light from the semiconductor light source(s) can radiate away from the body of the catheter. An electrical energization arrangement extends along the length of the body from the proximal region to the array, for energizing at least some of the semiconductor light sources of the array. The light sources of the array may be coupled in parallel, series, or series-parallel. In order to render the illumination of the walls of the vas more uniform, a dispersive element may be used, such as a frosted coating, which may be provided by sapphire powder, or by use of intralipid solutions of various concentrations. Preferably, the energization arrangement provides for independent energization of various portions of the light array. A balloon may be associated with the distal region of the catheter. Such a balloon has a membrane which is at least translucent to the light produced by the semiconductor light sources, whereby light radiated away from the semiconductor body in the distal region can pass through the membrane of the balloon to impinge on the walls of the vas. The balloon may provide the optical dispersion. This catheter also includes a balloon inflation lumen extending from the proximal region of the catheter to the balloon, so that the balloon may be inflated within the vas. Inflation of the balloon tends to flatten folds in the wall of the vas, and energization of the semiconductor light sources allows light to reach the wall of the vas. In the presence of a fluorescent photosensitive substance in the wall of the vas, the light reaching the wall of the vas results in fluorescence of the photosensitive substance. The catheter further includes a fluorescence light pickup and transmission arrangement located in the distal region, for picking up the fluorescence light, and for carrying a signal responsive to the fluorescence light to the proximal region, and for making the signal responsive to the fluorescence light available at the proximal region of the catheter. This fluorescence light pickup and transmission arrangement may comprise a photosensor such as a photodiode associated with the distal region of the catheter, for receiving the fluorescence light, and for generating an electrical signal in response to the fluorescence light, and some arrangement for conducting the electrical signal to the proximal end of the catheter. As an alternative, the fluorescence light pickup and transmission arrangement comprises an optical fiber extending from the distal region to the proximal region of the catheter. For this purpose, the distal end of the optical fiber is adapted for receiving a portion of the fluorescence light, and for coupling the portion of the fluorescence light into the optical fiber, whereby the portion of the fluorescence light in the optical fiber is the signal responsive to the fluorescence light. In a particular embodiment, the distal end of the optical fiber is made into an approximately spherical shape.

BRIEF DESCRIPTION OF THE DRAWING

FIG. 1 is a simplified illustration of a catheter according to an aspect of the invention;

FIG. 2a is a simplified cross-sectional side elevation view of the distal portion of the catheter of FIG. 1, illustrating a light flux sensor.

FIG. 8b is a simplified representation of a catheter with yet different equipment than that of FIG. 8a;

FIG. 9a is similar to FIG. 8a, but the m radiators and pickup devices are placed on a balloon, FIGS. 9b and 9c are developed views illustrating possible relative distal/proximal locations for the radiators and sensors, and FIG. 9d is similar to FIG. 8b;

DESCRIPTION OF THE INVENTION

Figure 4A:
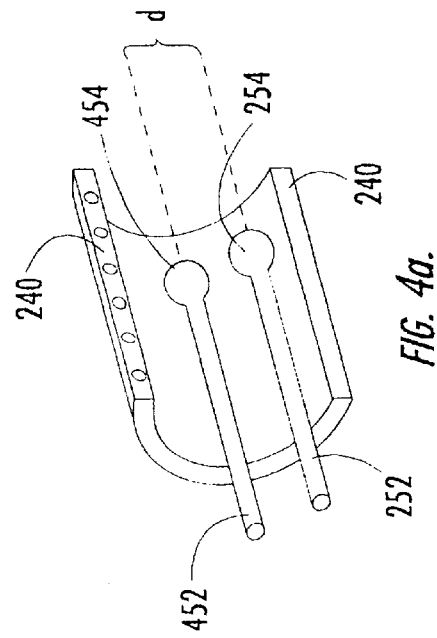
FIG. 4a is a representation of two optical fibers with radiative terminations of any sort located close to each other, for transmission of an illumination light pulse into the body by means of one, and for sensing the resulting fluorescence light with the other.

FIG. 1 is a simplified illustration of a catheter according to an aspect of the invention. In FIG. 1, a catheter 10 includes an elongated, generally flexible body 12 defining a distal end 14 and a proximal end 16. A portion 18 of catheter 10 near distal end 14 bears an inflatable balloon 20, illustrated in its deflated condition. Near the proximal end 16 of the catheter 10, various connectors, designated together as 22, provide access to various lumens, electrical and other paths associated with the catheter 10. For example, a connector of set 22 of connectors may provide access to a balloon inflation lumen (not illustrated in FIG. 1), while another connector of the set 22 may provide access to a set of electrical conductors (not illustrated) which carry power to semiconductor light sources located within the catheter. A local axis 8 extends along the centerline of the flexible catheter 10. A local axis is one which is locally straight, but which follows the contour or flexure of the flexed catheter.

FIG. 2a is a simplified cross-sectional side elevation view of the distal portion 14 of the catheter of FIG. 1, illustrating the membrane 20m expanded by inflation of the balloon 20. In FIG. 2a, a dielectric, or possibly metal, tube 210 extends through a lumen 212 defined within catheter body 12, and is spaced away from the inner surface 12is of body 12 by spacers 214 placed at various locations along the length of catheter 10. That portion of lumen 212 which lies between the inner surface 12is of lumen 212 in body 12 and the outer surface 210os of dielectric tube 210 is available for the flow of balloon inflation fluid, and is termed a "balloon inflation lumen" 212L. Dielectric tube 210 defines a central lumen 210L for the flow of coolant fluid. Coolant fluid flowing from proximal end 16 (FIG. 1) to distal end 14 of catheter 10 may exit from the catheter at a distal port 24, visible in both FIGS. 1 and 2a. The coolant fluid should be biocompatible if it is to be discharged into the patient's body. In another possible embodiment (not illustrated), the coolant fluid, instead of being discharged into the patient's body, may be routed back to the proximal end of the catheter through an additional lumen (not illustrated) or through the balloon inflation lumen 212L, whereupon the balloon would be inflated with the cooling fluid rather than with air.

Figure 2B:
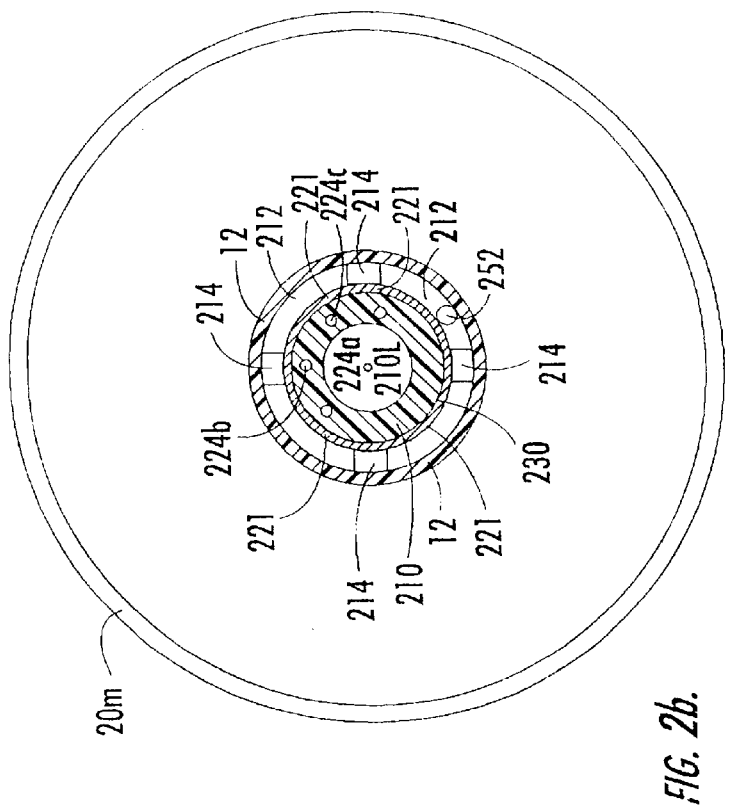
FIG. 2b is a cross-sectional view taken transverse to the local axis of FIG. 2a at a plane 2b—2b.

In the arrangement of FIGS. 2a and 2b, an array 220 of semiconductor light sources, some of which are designated 221, are mounted on the outer surface 210os of dielectric tube 210. The light sources are mounted so that, when energized, the light is directed in a radially outward direction relative to local axis 8. The semiconductor light sources of array 220 are electrically interconnected in known parallel, series, or series-parallel manner with one or more electrical conductors, illustrated as a set 224 of wires 224a, 224b, and 224c, which extend from the array 220 to one of the connectors 22 at the proximal end of the catheter 10 (FIG. 1). Wires 224a, 224b, and 224c are illustrated as extending through the body of dielectric tube 210, so that the body of the tube and the electrical insulation of the wires is integrated, to save space and complexity. As known to those skilled in the art, the various wires of set 224 may have electrical power applied to them in various combinations, to thereby separately energize various ones of the semiconductor light sources 221 or subarrays of the sources 221 of array 220. A transparent protective tube 230 extends over the array 220 of semiconductor light sources, in order to protect the light sources in the event that the inflation fluid should be a liquid or corrosive (or otherwise harmful) gas. This protective tube may be optically dispersive, as by the use of sapphire powder, by the use of intralipid solutions, or by other means. In one embodiment of the invention, a 1% intralipid solution was found to be effective in tending to make the illumination from the array 220 uniform. With the arrangement illustrated in FIGS. 2a and 2b, energization of one or more of the light sources 221 of array 220 results in emission of light directed away from local axis 8. The body 12 of catheter 10 is transparent, at least in the distal region near the array 220. The light generated by those sources 221 of array 220 which are energized penetrates through transparent layers 230 and 12, and, so long as the membrane 20m of balloon 20 is not opaque, also passes through the membrane to impinge on the walls 240 of a patient's vas. Any one, any combination, or all, of the three transparent layers 230, 12, and 20m may be translucent rather than transparent, to thereby tend to more evenly distribute light over the interior of the vas. In the particular case of treatment of BE, the vas is the esophagus.

According to an aspect of the invention, a light sensing arrangement designated generally as 250 is associated with catheter 20. In the arrangement of FIGS. 2a and 2b, light sensing arrangement 250 includes an optical fiber 252 extending from a connector of set 22 of connectors (FIG. 1) to the distal region, terminating in a light pickup probe 254. In FIG. 2a, light pickup probe 254 is merely a continuation or termination of optical fiber 252, formed into a roughly spherical shape for omnidirectional coverage. Those skilled in the art will recognize that the optical fiber may require cladding to reduce losses, and that the term as used herein includes such cladding if necessary or desirable. In accordance with another aspect of the invention, a photosensitizer such as 5-aminolevulinic acid (ALA) is administered to the patient, either orally, by injection, or topically, before the catheterization and phototherapy. Photosensitizers in general have the characteristic that they fluoresce when activated by illumination at particular wavelengths. More specifically, the photosensitizer 5-aminolevulinic acid (ALA) has the characteristic that, when it is illuminated at a wavelength in the vicinity of $5 (10^{-7})$ meters, or more specifically at 630 nm, it fluoresces, producing fluorescence light at a variety of wavelengths. The fluorescence is an indication that the medication has taken on an energized state, in which it interacts with molecular oxygen to form cytotoxic oxygen species. Instead of ALA, any of a number of photosensitizers could be used, with appropriate excitation.

The amount of fluorescence light depends, in part, upon the concentration of ALA or other photosensitizer in the patient's tissues in the illuminated region, and also depends in part on the absorbed portion of the illumination flux. The instantaneous fluorescence light amplitude, then, represents the instantaneous magnitude of the photodynamic therapy, and the integrated value of the fluorescence light over the duration of the treatment represents the total photodynamic therapy. That portion of the incident illumination flux which is not absorbed by the tissues is reflected in a nonspecular or diffuse manner, and adds to the incident illumination flux at another location. Thus, the incident illumination flux may, in general, be expected to arrive from many directions, and not necessarily only from the direction of the source of illumination flux. The fluorescence light produced by activation of the photosensitizer is picked up by spherical probe 254 of FIG. 2a and is coupled into optical fiber 252, in which the light propagates to the proximal end 16 of the catheter 10. At the proximal end, conventional optical filtration techniques can be used to separate the phototherapy illumination flux generated by the array 220 of light sources (together with reflected illumination flux) from the fluorescence light generated by illumination of the photosensitizer-treated tissues.

Figure 3A:
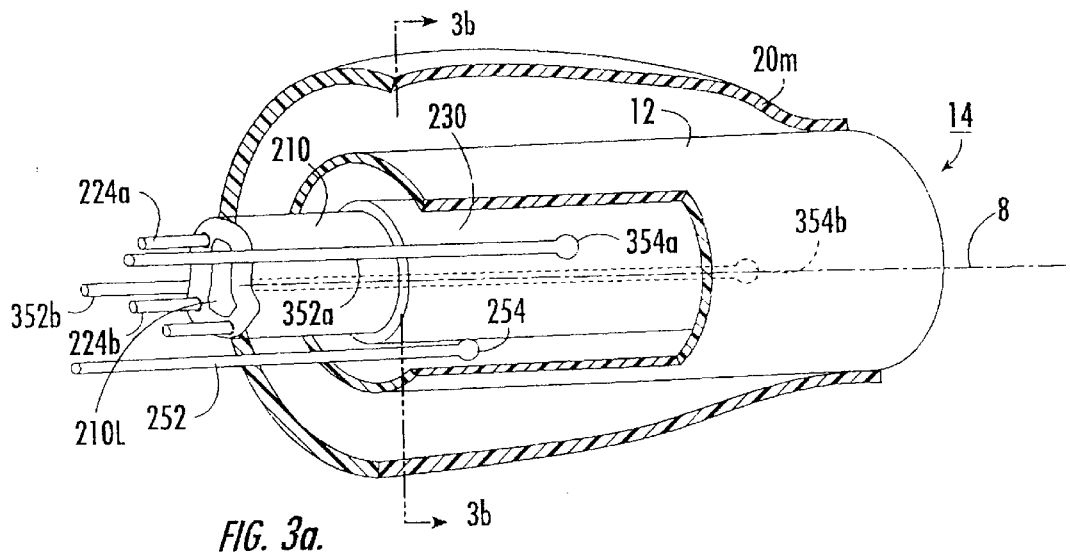
FIGS. 3a and 3b are simplified diagrams of an arrangement similar to that of FIGS. 2a and 2b, illustrating the use of plural light flux sensors.
Figure 3B:
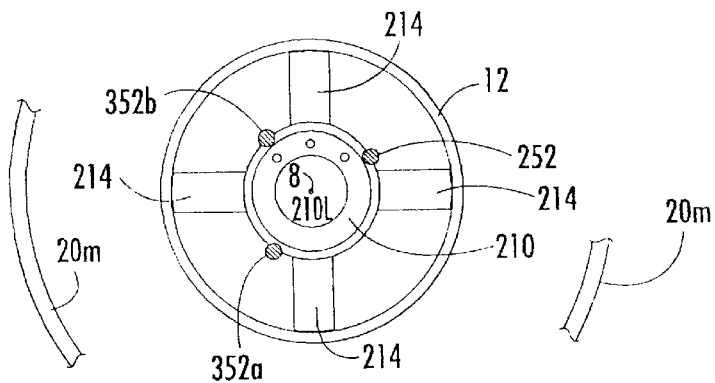

FIGS. 3a and 3b illustrate a catheter similar to that of FIGS. 2a and 2b, but including three spherical probes and optical fibers, with the probes being at different transverse planes along the length of the catheter. Elements of FIGS. 3a and 3b corresponding to those of FIGS. 2a and 2b are designated by like reference numerals or designations. In FIGS. 3a and 3b, in addition to spherical probe 254 and its associated optical fiber 252, two additional probes 354a and 354b are angularly spaced around the local axis 8 relative to probe 252, and the additional probes 354a, 354b are connected to optical fibers 352a and 352b, respectively. The optical fibers 352a and 352b are capable of carrying light in either direction, that is to say from without (outside of) the body of a patient to within, or from within the body of a patient to the external world. In one particular use, the optical fibers 352a and 352b carry samples of the light flux in the vicinity of the probes to locations without the patient. The light signals are available at appropriate connectors of set 22 of connectors near the proximal end of catheter 10 of FIG. 1. It should be noted at this point that the spherical probes will pick up any light flux in their vicinity, whether the result of fluorescence or reflection by the tissues, or the result of radiation by the semiconductor light sources of array 220. A sample of the light, from whatever source, will be transmitted through the associated optical fiber to the proximal end of the catheter.

Figure 4B:
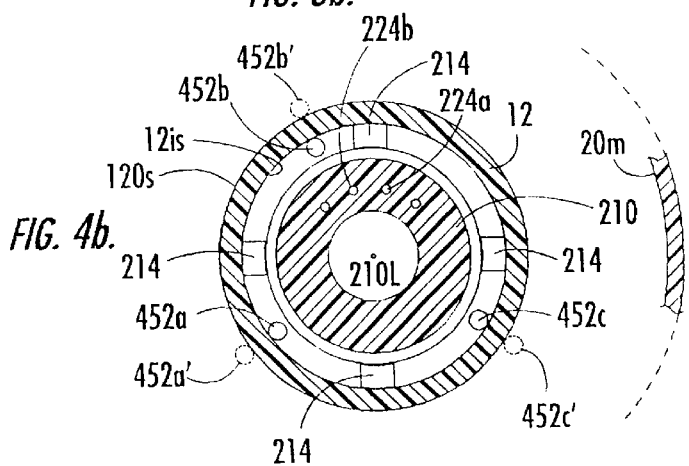
FIG. 4b is a cross-section of a portion of a catheter similar to those of FIGS. 2a, 2b, 3a, and 3b, in which three optical fibers are supported on the interior wall of the catheter body.

While the light probes of FIGS. 2a, 2b, 3a, and 3b are illustrated as being supported on dielectric tube 210, they could as easily be supported on the interior or exterior surface (or both, if desired) of body 12. FIG. 4b is a highly simplified transverse cross-section of a portion of a catheter similar to those of FIGS. 2a, 2b, 3a, and 3b, in which three optical fibers 452a, 452b, and 452c are supported on the interior wall 12is of the catheter body 12. The spherical probe ends are not illustrated in FIG. 4b. Also illustrated in phantom in FIG. 4b are alternative support locations 452a', 452 b', and 452c' for the optical fibers, which are on the outer surface 12os of the body 12. For the sensing of fluorescence, supporting the probes and their associated optical fibers on the exterior surface 12os of body 12 interposes the least physical structure, namely the balloon membrane 20m, between the probes and the source of the fluorescence, which is the patient's tissues adjacent the outer surface of balloon membrane. By contrast, if the probes are intended to measure the flux produced by the semiconductor light sources of array 220 of FIG. 2a, the probe and optical fiber location illustrated in FIGS. 2a, 2b, 3a, and 3b is close to optimum, because only the transparent cover 230 lies between the probe and the light source array, so that the direct illumination flux will be sensed, and illumination flux reflected from the tissues and contributing to the overall illumination flux will also be sensed. It should be noted that, for the sensing of tissue fluorescence, a mounting location on the balloon membrane 20m itself might be appropriate.

Figure 5:
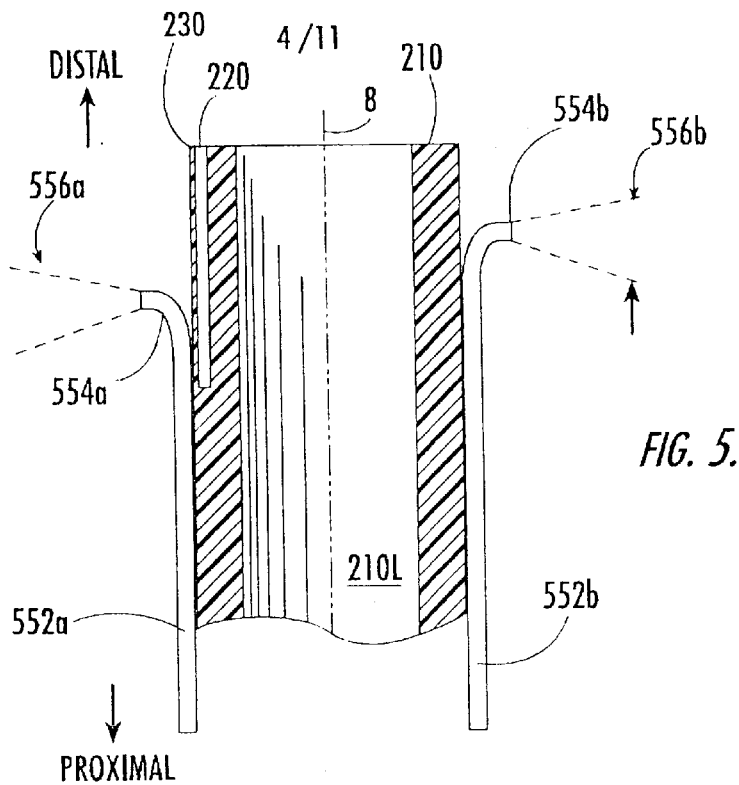
FIG. 5 is a highly simplified diagram of a portion near the distal end of a catheter, illustrating light flux probes which are directional.

FIG. 5 is a highly simplified diagram of a portion near the distal end of a catheter, illustrating light flux probes which, unlike the spherical probes illustrated in conjunction with FIGS. 2a, 2b, and 3a, are directional. In FIG. 5, the probes 554a and 554b are illustrated as being mounted on the exterior surface of dielectric tube 210. Each probe consists essentially of an end portion of an optical fiber which has its optical axis directed radially away from local axis 8. In FIG. 5, probes 554a and 554b are merely the extensions of bent portions of optical fibers 552a and 552b. In general, an abruptly terminated optical fiber will "radiate" to some degree, where the term "radiate" has a meaning similar to that ascribed to it in the antenna arts, namely as including both transmission and reception. An abrupt termination is not optimum for radiation, and many ways are known to increase the radiation efficiency, including the use of transparent layers of various dielectric constants over the radiating aperture, tapering the fiber, and the like. In any case, the radiation can be caused to be directional. The bends in the optical fibers as illustrated in FIG. 5 are selected to cause the probes 554a and 554b to receive light arriving at the probe in a roughly radially-inward direction over a cone (or other shape) in space illustrated as 556a and 556b, respectively. Such a directional response will tend to reduce the amount of light radiating in a radially-outward direction which is picked up by the probe, which in more practical terms means that such an inwardly-sensitive probe will tend to pick up fluorescence light (and, unavoidably, reflected illumination light) rather than semiconductor-source illumination light.

Figure 6:
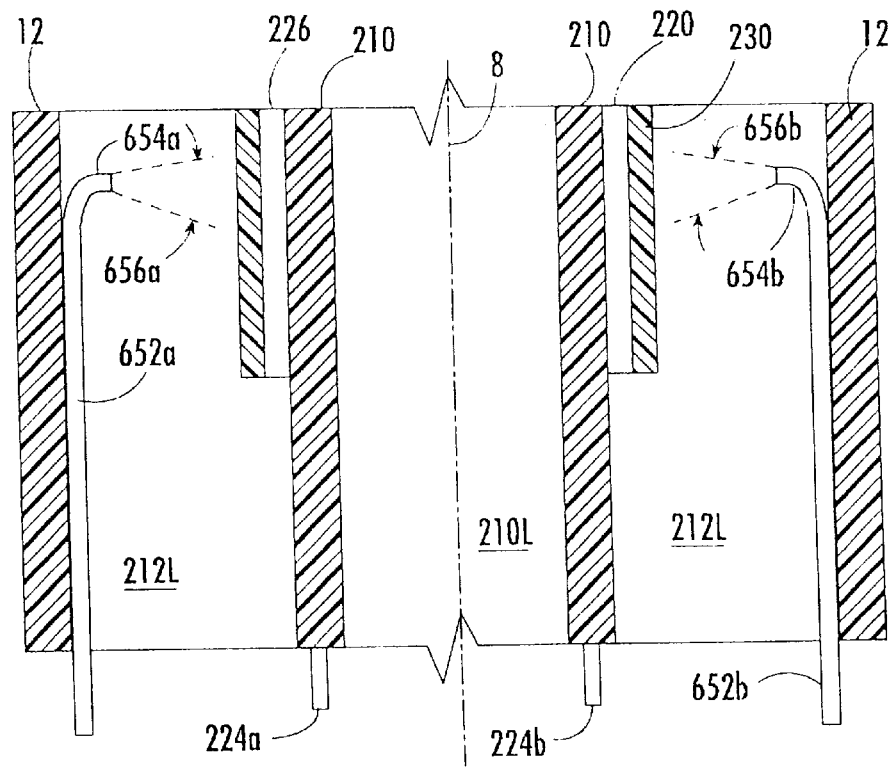
FIG. 6 is a simplified longitudinal cross-sectional view near the distal end of another catheter, illustrating the use of two probes having inwardly-directed radiating patterns.

FIG. 6 is a simplified longitudinal cross-sectional view near the distal end of another catheter, illustrating the use of two probes having directional radiating patterns, where the radiation patterns are directed radially inward, to respond to the light flux from the semiconductor light source array 220. In FIG. 6, the light probes 654a and 654b are essentially bent portions of optical fibers 652a and 652b, respectively. Because of the direction of the axis of the terminating or radiating portion of the fiber, the cones 656a and 656b, representing the angles through which probes 654a and 654b, respectively, preferentially receive radiation, is directed toward a portion of semiconductor light source array 220. This preferential reception tends to reduce the amount of light received in a radially-inward direction. Thus, it is possible with a spherical probe to respond to essentially the same degree to light radiation flowing radially inward or outward, or with a directive probe to respond preferentially to radially-inward (fluorescence light) or radially-outward (light source array light) light flux.

As so far described, the light sensors have been described as probes which sample the light flux in the region of the probe, and conduct the sample to the proximal end of the catheter, where the samples become available. At the proximal end of the catheter, the doctor or medical technician may use spectrum analysis to distinguish between the light arising from fluorescence and that originating from the semiconductor light source array. The amplitude of the light from the light source array may be useful in maintaining proper operation of the array, and in changing the excitation to maintain constant, increase or decrease the magnitude of the applied light flux, as may be desired. The magnitude of the light flux attributable to fluorescence of the photosensitive medication, however, can be used to monitor and or control the dose of photodynamic therapy.

The magnitude of the fluorescence depends on several variables, including the concentration of the photosensitive medication in the irradiated region, the applied light flux, and the magnitude of the absorbed (as opposed to reflected) light flux. The applied light flux and the duration of the treatment can be varied in dependence upon the sensed values. If the concentration of the medication happens to be low, increasing the concentration of medication, or increasing the duration of the application of a particular light flux, or increasing the magnitude of the applied flux applied for the originally estimated time, may all act to countervail the original problem of low concentration of medication. The time integral of the magnitude of the fluorescence light flux is a proxy for the photodynamic therapy dose. The doctor or medical technician may use the signal from incident light during treatment and integrate over time to determine the total light delivery or integrated flux. In addition, he may at any time use the fluorescence signal from the wall of the vas, obtained by a pulse of light applied through a first probe at a particular wavelength or band of wavelengths, as measured at a second probe located adjacent the first probe, to determine the amount of photosensitizer in the wall of the vas. Intermittent measurements over time of fluorescence may thus be used to provide a measure of the tissue concentration of photosensitizer during phototherapy.

The ALA or other photosensitizer may be administered to the patient orally, topically, or by injection. After a suitable interval, if needed, for the patient to absorb the dose, the catheter is introduced, and the light source array is activated. The incident or applied illumination light flux from the array (or other light source) may be monitored. Simple integration over time provides an indication of the light dose. Similarly, the fluorescence flux resulting from the phototherapy may be monitored, and integrated over time to provide a direct measure of the phototherapy dose. The monitoring may be by a simple photodiode associated with the proximal end of each of the optical fibers associated with the light probes. The photodiode produces an electrical signal which is an analog of the illumination light flux or the fluorescence flux, or both, depending upon the wavelength filters which are used. Simple integration of the electrical signal over time produces a signal which is related to the total phototherapy dose. Such integration is notoriously well known in the electrical fields, and requires no additional explanation. In the most simple case, the phototherapy is continued until the desired dose, represented by the achieving of a particular integrated value, is achieved. If it should be found that the progress is too slow, the amount of medication may be increased, or the source light flux may be increased, to increase the rate of phototherapy.

Since there may be several probes in the vicinity which is subject to phototherapy, it may be that no one probe is totally representative of the overall dose. In that situation, it may be desirable to average the doses represented by the integrated signals. Another way to handle that situation is to associate one light probe with one section of the light source array, and to treat each portion as an independent entity; thus, when one probe indicates that the dose for a particular portion of the region to be treated has been achieved, the portion of the light source array associated with that region is turned off, while other portions of the light source array remain on to continue phototherapy of the regions where the full dose has not been achieved.

Figure 7:
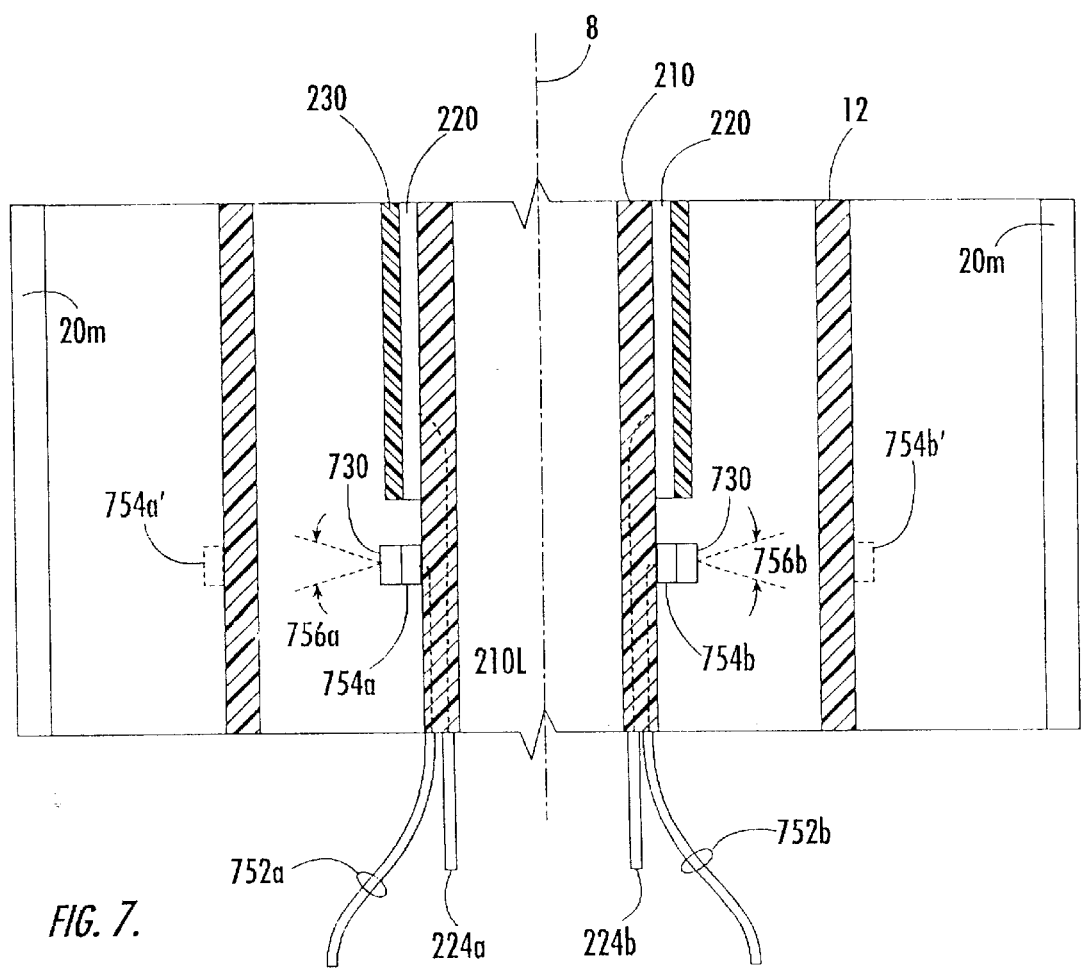
FIG. 7 represents a portion of the distal end of a catheter according to this aspect of the invention, in which solid-state photosensors are mounted on the exterior surface of the dielectric tube.

According to another aspect of the invention, the light probes associated with the catheter may be semiconductor sensors, such as photodiodes. In this aspect of the invention, recognizing that in the abovedescribed embodiments the light is taken outside of the body and applied to a photodiode, the photodiode(s) are instead placed inside the probe, and an electrical signal is taken from the distal end of the catheter to the proximal end. FIG. 7 represents a portion of the distal end of a catheter according to this aspect of the invention. In FIG. 7, elements corresponding to those of FIGS. 2a and 2b are designated by like reference numerals. In FIG. 7, solid-state photosensors, designated 754a and 754b are mounted on the exterior surface of the dielectric tube 210. Each has a transparent protective cover 730. Each photosensor 754a and 754b responds to light impinging thereon within a cone 756a and 756b, respectively, by producing an electrical signal on a conductor set 752a and 752b, respectively. The cone angles are such that light travelling radially outward tends to be rejected, and light within the cone angles and travelling radially inward tends to be accepted. Thus, instead of the light signal being in the form of a sample of the actual light as in FIGS. 2a, 3a, 4, 5, and 6, the light signal in the case of FIG. 7 is in the form of an equivalent electrical signal. An alternative location for the photosensors is illustrated in phantom as 754a' and 754b' in FIG. 7.

Instead of being outside the longitudinal region of the light source array 220 as described in conjunction with FIG. 7, the light flux sensor, whether a light probe or a photosensor, may be essentially co-located with the light source array. Of course, two devices cannot physically occupy the same space, so they may be interleaved if lying in the same plane.

Figure 8A:
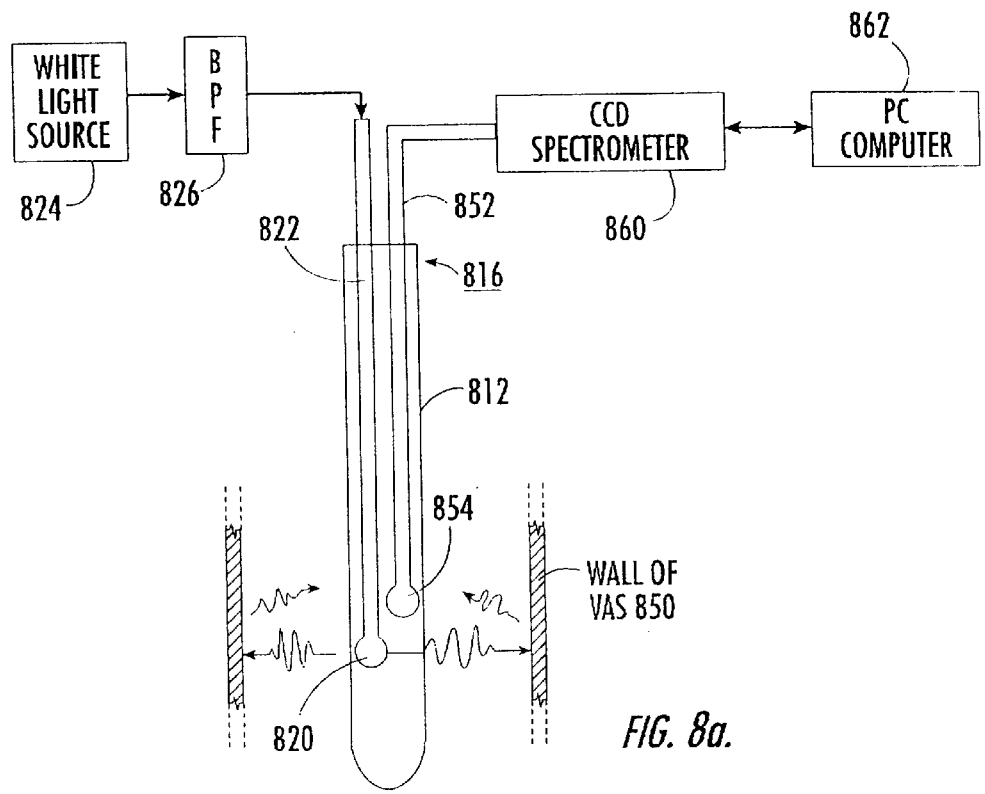
FIG. 8a is a simplified representation of a catheter with other equipment, in accordance with an aspect of the invention, for providing light to omnidirectional radiators and pickup devices or sensors.
Figure 8B:
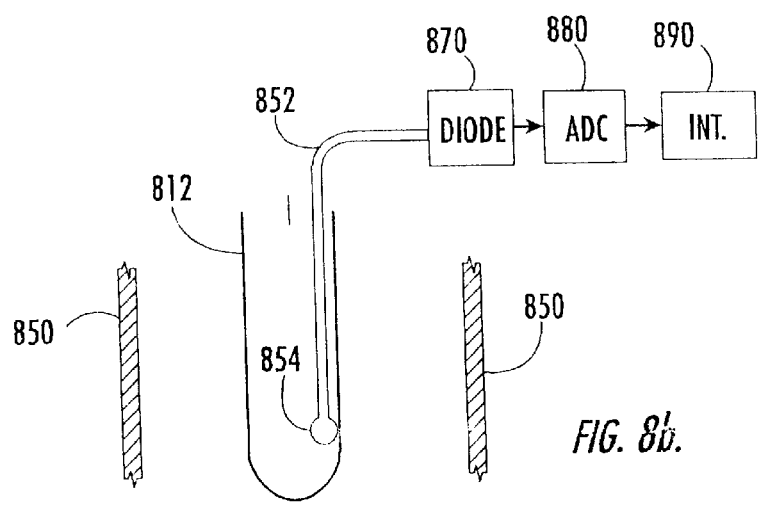

In yet another embodiment of a catheter according to an aspect of the invention, the light source includes a source of white light, accompanied by an optical filter to provide the desired wavelength of the phototherapy light. In the embodiment of FIG. 8a, the photodynamic therapy apparatus is designated as 810, which includes a catheter 812. Catheter 812 includes various lumens, balloon membranes, conductors and the like, as may be required. In addition, catheter 812 includes a first "omnidirectional" light source 820, which is similar to a spherical light probe described above. Light source 820 is coupled to an optical fiber 822, which extends through the length of the catheter 812 to its proximal end 816. A white light source illustrated as a block 824 produces white light. The white light is applied to an optical bandpass filter (BPF) illustrated as a block 826. Filter 826 transmits a particular band of wavelengths, such as a band centered at 630 nm, and the band of light is applied to the proximal end of optical fiber 822. The light in the desired band is transmitted along the fiber to the omnidirectional head, and is radiated more or less uniformly toward the walls of the vas, illustrated in FIG. 8a as 850. The fluorescence may be sensed in any appropriate manner, as with a further spherical probe 854 connected to an optical fiber 852. The sensed light is transmitted over optical fiber 852 to the proximal end of the catheter. At the proximal end, the light is coupled from the proximal end of the light fiber 852 to a spectrometer, which in one embodiment is a CCD spectrometer, consisting of a grating spectrograph and a high-resolution camera, in which data acquisition and analysis are controlled by a computer 862. Such an apparatus can be calibrated by placing the active portion of the catheter into a tissue equivalent phantom with known optical properties and known concentration of photosensitizer, and measuring the fluorescence signal in response to activation with the source light system including the white light source 824 and bandpass filter 826. The arrangement of FIG. 8b is similar to that of FIG. 8a, but the sensing arrangement includes light sensor 854, optical fiber 852, and an apparatus at the proximal end fiber 852 including a photodiode 870, and analog-to-digital converter 880, and an integrator 890. Although not illustrated in FIG. 8b, the light from optical fiber 852 may be filtered in a wavelength-dependent filter before application to diode 870, to reject either the fluorescence light or a principal portion of the illumination or incident light. The light sample, whether filtered or not, is applied to photosensor 870 to convert the light into electrical signal. The electrical signal is converted into digital form in ADC 880. The digital signal is integrated in integrator 890, which generates the integrated signal representative of the changes in photosensitizer concentration, light dose, and or cumulative dose of phototherapy at the location of the probe 854. The position of probe 854 along the length of the catheter may be selected, and multiple locations may be simultaneously sampled by the use of a plurality of sensors and optical fibers. Instead of the probe(s) 854 and its (their) associated fiber(s) 852, a photodiode located within the catheter could be used at each location, as described above.

In FIG. 9a, catheter 812 includes various lumens, balloon membranes, conductors and the like, as may be required. In addition, catheter 812 includes a first "omnidirectional" light source 920, which is similar to a spherical light probe described above. Light source 920 is coupled to an optical fiber 922, which extends through the length of the catheter 812 to its proximal end 816. A white light source illustrated as a block 824 produces white light. The white light is applied to an optical bandpass filter (BPF) illustrated as a block 826. Filter 826 transmits a particular band of wavelengths, such as a band centered at 630 nm, and the band of light is applied to the proximal end of optical fiber 922. The light in the desired band is transmitted along the fiber 922 lying along the body of catheter 812 and the inflated balloon membrane 20m to the omnidirectional head 920, which is illustrated as being mounted on the exterior of balloon membrane 20m. The fiber 922 and head 920 could as easily lie on the inside surface of balloon membrane 20m. The light is radiated from head 920 more or less uniformly toward the walls of the vas, illustrated in FIG. 9a as 850. The light radiated from head 920 activates the photosensitizer in the tissues of the vas, resulting in fluorescence. The fluorescence may be sensed in any appropriate manner, as with a further spherical probe 954 connected to an optical fiber 952, also lying on the exterior (or alternatively the interior) of the membrane 20m and catheter body. The sensed light is transmitted over optical fiber 952 to the proximal end of the catheter. At the proximal end, the light sample may be spectrum analyzed in a block 860 as described in conjunction with FIG. 8a. In another embodiment illustrated in FIG. 9d, optical fiber 952 is coupled to a photodiode 870, ADC 880, and integrator 890, as described in conjunction with FIG. 8b.

FIG. 9b represents the balloon membrane 20m of FIG. 9a, developed to illustrate the locations of plural light radiating and or sensing heads, which may be used for either fluorescence or incident light. In FIG. 9b, radiating heads 920a, 920*b*, and 920*c* (representative of all the radiating heads about the balloon membrane) are fed from their respective optical fibers 922*a*, 922*b*, and 922*c*. Between each radiating head and the next is a light pickup or sensing head, such as head 954 of FIG. 9*a*. In FIG. 9*b*, the sensing heads are designated 954*a* and 954*b*, which feed their respective optical fibers 952*a* and 952*b*. The relative locations of the radiating heads is more distal than the sensing heads.

FIG. 9*c* represents the balloon membrane 20*m* of FIG. 9*a*, developed to illustrate alternative locations of plural light radiating and sensing heads. In FIG. 9*c*, radiating heads 920', 920", and 920'" (representative of all the radiating heads about the balloon membrane) are fed from their respective optical fibers. Between each radiating head and the next is a light pickup or sensing head, such as head 954 of FIG. 9*a*. In FIG. 9*c*, the sensing heads are designated 954', 954", and 954'", which feed their respective optical fibers. The relative locations of some of the radiating heads is more distal than the sensing heads, and others are more proximal. It should be noted that measurement of fluorescence by the sensing heads located at various distances from the radiating head, performed either before or after administration of photosensitizer, by applying light to the radiating heads while monitoring the fluorescence at the sensing heads, may help to determine the light propagation properties, such as attenuation coefficient, of the tissue being treated by phototherapy.

In the arrangements of FIGS. 8 and 9*a*, the light sensing heads can alternatively be used to measure the strength of the incident light radiated by the light radiating heads.

Figure 10:
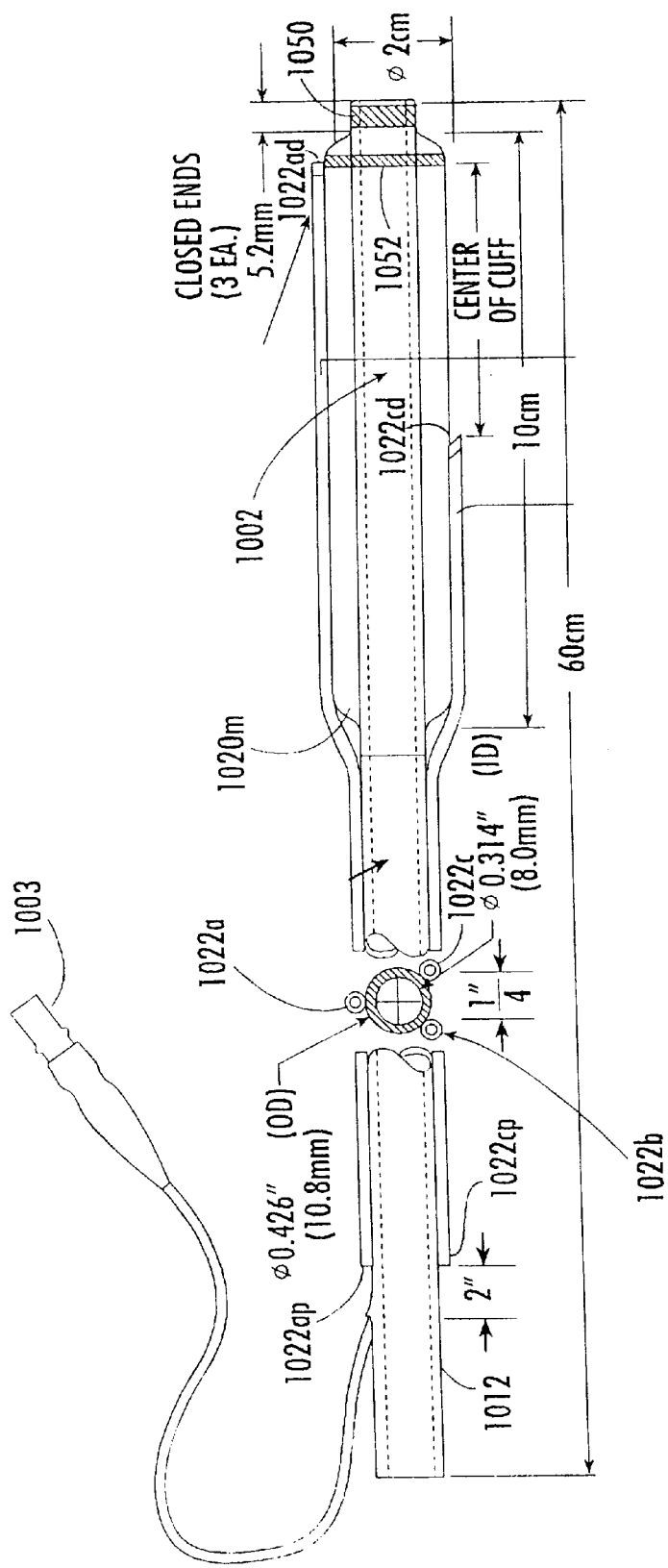
FIG. 10 is a simplified side or elevation view of a catheter according to an aspect of the invention, with a cross-sectional representation along the length of the catheter body.

FIG. 10 is a simplified side or elevation view of an incomplete catheter according to an aspect of the invention, with a cross-sectional representation along the length of the catheter body. In FIG. 10, the catheter body or esophageal tubing is designated 1012, and the external portion of the balloon inflation tube is designated 1003. The balloon membrane is designated 1020*m*. 1002 represents the cuff of the catheter. Three pieces of flexible tubing 1022*a*, 1022*b*, and 1022*c* are attached, with tubing 1022*a* being at the top of the structure, as illustrated in the cross-sectional representation, and the other two being equally placed around the body 1012. These pieces of tubing should be dimensioned to allow passage of a 0.040" diameter optical fiber, and should have a larger diameter if an enlarged end is provided on the optical fiber. The proximal ends 1022*ap*, 1022*cp* of the flexible tubes is open, to allow the optical fibers to be inserted, while the distal ends 1022*ad* and 1022*cd* are closed. The tubes 1022*a*, 1022*b*, and 1022*c* could be replaced, if desired, by channels defined in the catheter and balloon for insertion of optical fibers. Such channels may also include electrical conductors, if desired, for ready electrical connection of photosensors. Annular position markings may be added at various locations, as for example 1050 at the distal tip of the catheter, 1052 at the distal end of the cuff, 1054 at the proximal end of the cuff, and 1056 at the proximal end of the balloon. Naturally, markings may be applied to the body 1012 of the catheter.

Figure 11A:
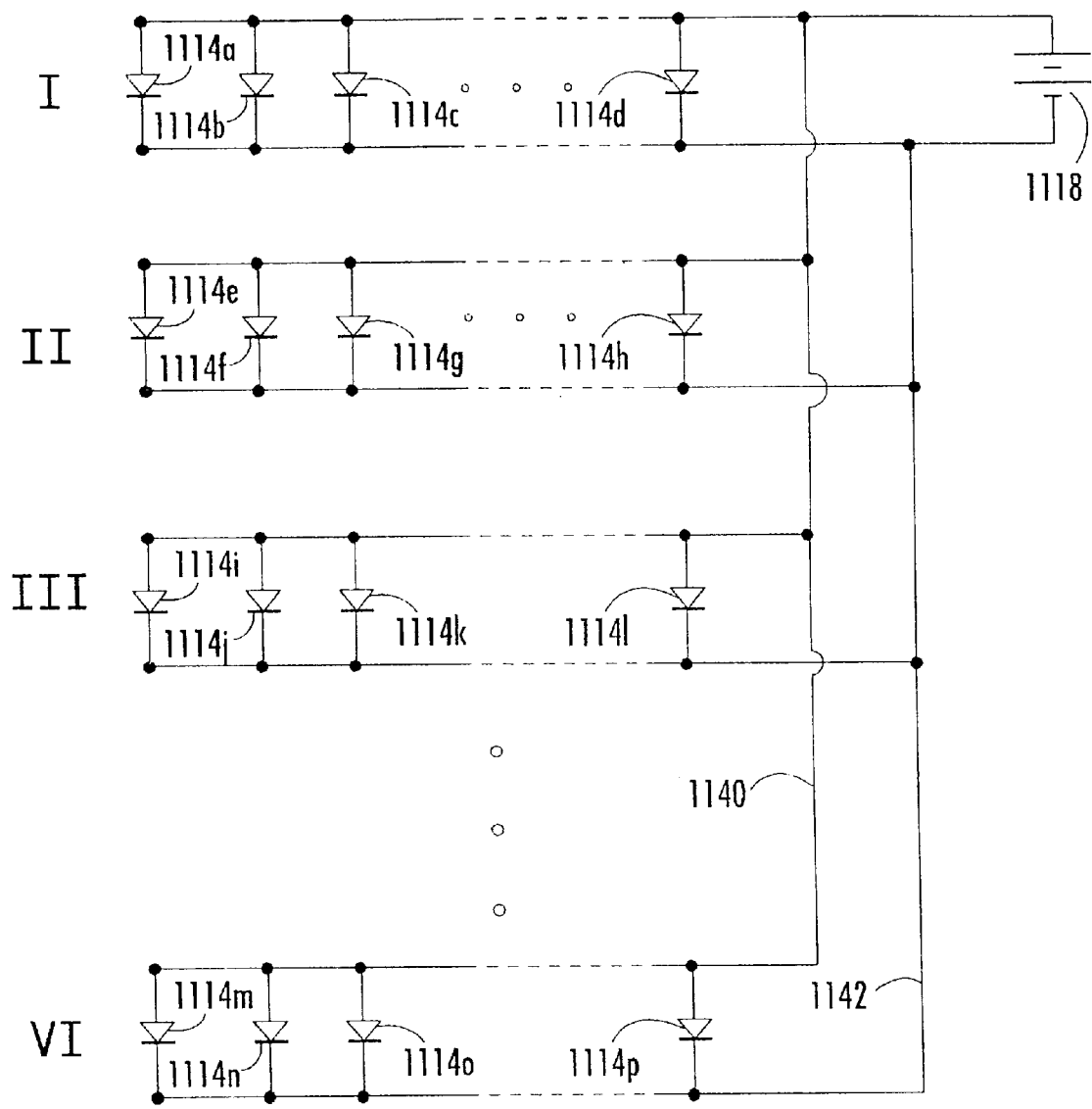
FIGS. 11a and 11b are schematic illustrations of electrical energization schemes for energizing semiconductor light sources of the arrangement of FIG. 2a in parallel and series-parallel, respectively.

FIG. 11*a* illustrates one type of electrical connection which can be made between a source of electrical energy, illustrated by a battery symbol 1118 and an array 220 of semiconductor light sources, illustrated by diode symbols. As illustrated therein, the light sources 1114*a*, 114*b*, 1114*c*, . . . 1114*d* are arranged in a first row I, light sources 1114*e*, 1114*f*, 1114*g*, . . . 1114*h* are arranged in a second row II, light sources 1114*i*, 1114*j*, 1114*k*, . . . 1114*l* are arranged in a third row III, and light sources 1114*m*, 1114*n*, 1114*o*, . .1114*p* are arranged in a last row designated VI. Electrical conductor 1140 connects the "anodes" of all of the light sources 1114 of array 220 to the positive terminal of battery 1118, while the electrical conductor 1142 connects the "cathodes" of all of the light sources to the negative terminal of the battery. With this arrangement, the full battery voltage appears across each of the light sources.

Figure 11B:
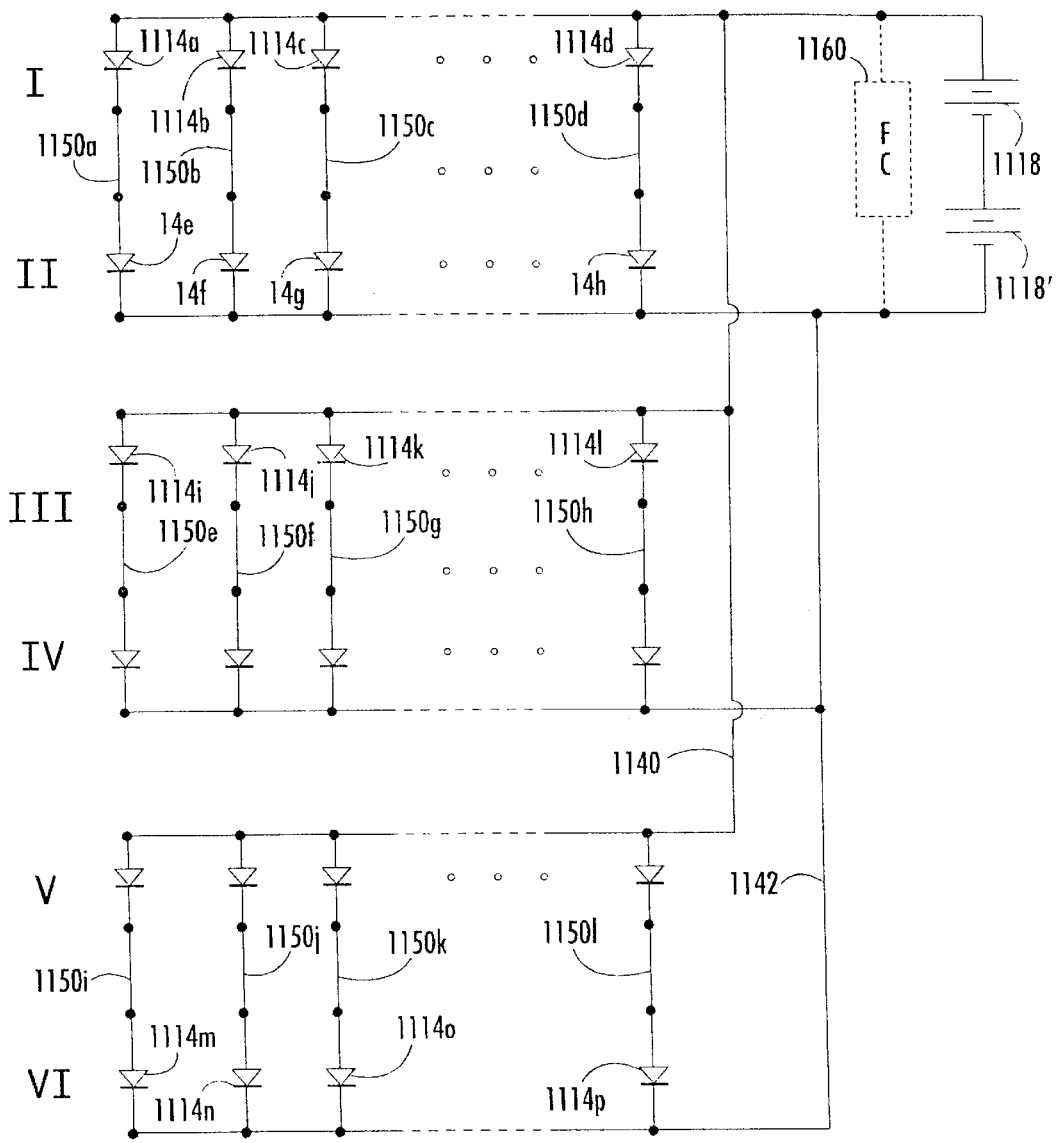

FIG. 11*b* illustrates another type of electrical connection which can be made among the light sources of array 220 and the battery 1118. In the arrangement of FIG. 11*b*, elements corresponding to those of FIG. 11*a* are designated by like reference numerals. In FIG. 11*b*, additional rows IV and V of semiconductor light sources are illustrated. Conductor 1140 is connected to the "anodes" of the light sources of rows I, III, and V, while conductor 1142 is connected to the "cathodes" of the light sources of rows II, IV, and VI. In addition, a set of electrical conductors 1150*a*, 1150*b*, 1150*c*, . . . 1150*c* individually connects the "cathodes" of light sources 1114*a*, 1114*b*, 1114*c*, . . ., 1114*d* to the "anodes" of light sources 1114*e*, 1114*f*, 1114*g*, . . ., 1114*h*, respectively. A further set of electrical conductors 1150*e*, 1150*f*, 1150*g*, . . . 1150*h* individually connects the "cathodes" of light sources 1114*i*, 1114*j*, 1114*k*, . . ., 1114*l* to the "anodes" of the light sources (not individually designated) of row IV. Similarly, a further set of electrical conductors 1150*i*, 1150*j*, 1150*k*, . . . 1150*l* individually connects the "cathodes" of the semiconductor light sources of row V to the "anodes" of the light sources 1114*m*, 1114*n*, 1114*o*, . . ., 1114*p* of row VI. Those skilled in the art will recognize this as a series-parallel electrical connection, which requires less total current from the electrical source, but, for equal power, requires double the applied voltage. In the arrangement of FIG. 11*b*, the additional voltage is represented by an additional battery designated 1118', illustrated as being connected in series with battery 1118. Those skilled in the art know that many different series-parallel connections are possible, to achieve almost any desired ratio of energization voltage to current. The selected ratio should be suited to the capabilities of the source of voltage, which in the illustrated arrangement is a battery. Instead of a battery as illustrated in FIG. 11*b*, the energization source could be a fuel cell, illustrated in dashed lines as 1160, or any other type of electrical source.

Figure 11C:
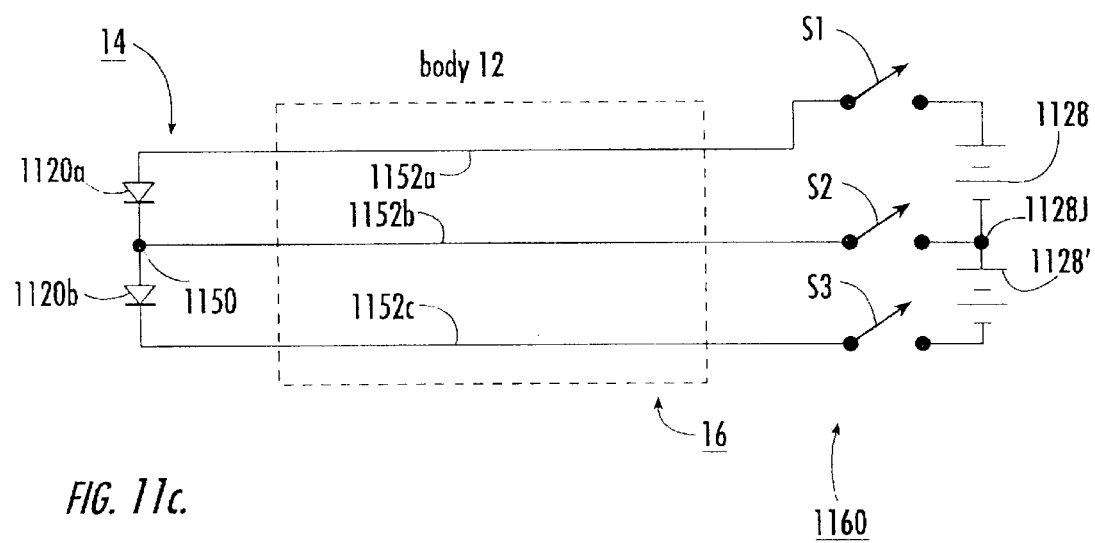
FIG. 11c is a simplified schematic illustration of an arrangement for energizing portions of the array of semiconductor light sources of FIG. 2.

FIG. 11*c* is a simplified schematic illustration of an arrangement for energizing portions of the array 220 of semiconductor light sources of FIG. 2. In FIG. 11*c*, a diode symbol 1120*a* represents an array of one or more electrically interconnected light sources, and 1120*b* represents another such array. The "cathode" of light source 1120*a* is connected to the "anode" of light source 1120*b* at a junction 1150. A first electrical conductor 1152*a* is connected to the "anode" of light source 1120*a*, and extends through at least a portion of catheter body 12 to exit or become available at the proximal end 16. A second conductor 1152*b* is connected to the junction 1150, and extends through at least a portion of catheter body 12 to exit or become available at the proximal end 16. A third conductor 1152*c* is connected to the "cathode" of light source 1120*b*, and extends through at least a portion of catheter body 12 to exit or become available at the proximal end 16. A switched electrical source arrangement designated generally as 1160 is coupled to conductors 1152*a*, 1152*b*, and 1152*c*, for energizing either or both light sources 1120*a* and 1120*b*. Switched source 1160 includes a first electrical source illustrated by a battery symbol 1128, and a second electrical source illustrated by a battery symbol 1128'. The anode of electrical source 1128' is connected to the cathode of source 1128 at a junction 1128J. Switched source 1160 also includes a first electrical switch S1 connected between conductor 1152*a* and the anode of electrical source 1128, a second electrical switch S2 connected between conductor 1152*b* and junction 1128J, and a third electrical switch S3 connected between conductor 1152*c* and the cathode of electrical source 1128'. Those skilled in the art know that electrical switches are ordinarily represented by mechanical switch symbols for simplicity, but that electronic or solid-state switches may be used instead. Also, those skilled in the art know that the word "between" as applied to electrical interconnections does not have a meaning of physical location, but instead refers to a type of electrical interconnection. In order to energize the light source array represented as 1120*a* but not the light source represented as 1120*b*, switches S1 and S2 are closed (rendered conductive), and switch S3 is left open (nonconducting). In order to energize the light source array represented as 1120*b* but not the light source represented as 1120*a*, switches S2 and S3 are closed, and switch S1 is left open. In order to energize both light sources 1120*a* and 1120*b*, switch S2 is left open and switches S1 and S3 are closed. Those skilled in the art will recognize that may different schemes are available for controlling the energization of various portions of the light source array.

Other embodiments of the invention will be apparent to those skilled in the art. For example, while embodiments have been illustrated having a single light flux probe and three light flux probes, any desired number may be used. The probes may be angularly distributed around the local axis, or not, as desired, and there may be more than one probe at any particular transverse plane. While the use of solid-state light sensors within the catheter has been described as an alternative to the use of light conductors to carry samples of the light flux to the exterior of the patient, both types may be used in the same catheter, if desired.

Thus, a phototherapy method according to the invention includes the step of administering a photosensitive medication to a patient, which medication fluoresces in response to light flux. Energy (electrical or light) is applied to a proximal end (16) of a catheter (10) adjacent tissue (240) of the patient, to thereby cause light flux from a distal end (14) of the catheter, whereby the light flux causes the photosensitive medication in the patient's tissues to fluoresce. A signal is generated which is representative of one of (which is to say, is either or both of) the light flux and the fluorescence. The signal so generated, which may be either in the form of a light sample or an electrical signal, is coupled by way of the catheter (10) to a location without (outside of) the patient. The signal may be analyzed to determine any of several parameters.

A phototherapy method according to another aspect of the invention includes the steps of administering a medication to a patient, which medication fluoresces within a specific range of wavelengths in response to light flux. Light flux is applied to a vas of the patient through a catheter, for thereby performing phototherapy, and also causing the medication to fluoresce in response to the flux. A signal (light sample from sensors such as 254 or electrical signal from diode(s) 754*a*, 754*b*) representing at least a portion of the fluorescent light is routed to a location without the patient by means of the catheter. The method includes the further step of establishing or determining (by integration of the instantaneous sample signal), from at least the fluorescence-representative signal, at least one of (a) the intensity of the applied flux and (b) the duration of the applied flux.

In a particular mode of the method of the invention, the step of determining from at least the fluorescence includes the step of determining or sensing at least one of the power or equivalently, the intensity or amplitude of the fluorescence. In a particular mode of the method, the step of administering medication includes the step of administering 5-aminolevulinic acid (ALA) orally. The medication may also be injected or administered topically. According to this particular mode, the step of applying light flux includes the step of applying a light flux having its peak amplitude at a wavelength at a particular wavelength, such as, for example, in the vicinity of $5$ ($10^{-7}$) meters. This may be accomplished, in one version, by generating white light (834), and passing the white light through an optical bandpass filter (826) having a peak in transmission response in the vicinity of $5$ ($10^{-7}$) meters.

In a preferred mode of practicing the method of the invention, the step of applying light flux includes the step of applying electrical excitation to a plurality (220) of semiconductor light sources (221) associated with a distal portion (14) of the catheter (10), which semiconductor light sources (220) produce light in the vicinity of $5$ ($10^{-7}$) meters.

The inventive method may also include, before the step of administering medication, the sensing of the fluorescence of the vas of the patient in response to a flux of light, to provide a normalization of the sensed light flux.

According to another aspect of the invention, a catheter (10) for phototherapy comprises an elongated body (12) defining an axis (8) of elongation, a distal region (14), and a proximal region (16), which distal region (14) is adapted for introduction into a vas (240) of a patient. An elongated array (220) of semiconductor light sources (221)is associated with the catheter body (12) near the distal region (14). The semiconductor light sources (220) and the body (12) near the semiconductor light sources are such that, when the light source(s) (220 or portions thereof) are energized, light from the semiconductor light source(s) can radiate away from the body (12) of the catheter. For this purpose, at least portions of the body and ancillary structures are transparent or translucent An electrical energization arrangement (224) extends along the length of the body (12) from the proximal region (16) to the array (220), for energizing at least some of the semiconductor light sources (221) of the array. Preferably, the energization arrangement (224) provides for independent energization (various sets of conductors 224*a*, 224*b*, 224*c*, . . .) of various portions of the light array (220). A balloon (20) may be associated with the distal region (16) of the catheter (12). Such a balloon (20) has a membrane (20*m*) which is at least translucent to the light produced by the semiconductor light sources (220), whereby light radiated away from the semiconductor light sources in the distal region can pass through the membrane (20*m*) of the balloon (20) to impinge on the walls (240, 850) of the vas. This catheter (10) also includes a balloon inflation lumen (212) extending from the proximal region (16) of the catheter to the balloon (20), so that the balloon (20) may be inflated within the vas. Inflation of the balloon (20) tends to flatten folds in the wall of the vas, and energization of the semiconductor light sources (220) allows light to reach the wall of the vas. In the presence of a fluorescent photosensitive substance in or on the wall of the vas, the light reaching the wall of the vas results in fluorescence of the photosensitive substance. The catheter further includes a fluorescence light pickup (254, 554*a*, 754*a*, 854) and transmission arrangement (252, 352, 452, 552, 652, 752*a*, 852) at least partially located in the distal region (16), for picking up the fluorescence light, and for carrying a signal (light sample or electrical analog thereof) responsive to the fluorescence light to the proximal region (16), and for making the signal responsive to the fluorescence light available at the proximal region of the catheter. This fluorescence light pickup and transmission arrangement may comprise a photosensor (754a) associated with the distal region (14) of the catheter (10), for receiving the fluorescence light, and for generating an electrical signal in response to the fluorescence light, and some arrangement (conductors 752a) for conducting the electrical signal to the proximal end (16) of the catheter (10). As an alternative, the fluorescence light pickup and transmission arrangement comprises an optical fiber (252, for example) extending from the distal region (14) to the proximal region (16) of the catheter (10). For this purpose, the distal end of the optical fiber is adapted (by a spherical or bent portion of the fiber) for receiving a portion of the fluorescence light, and for coupling the portion of the fluorescence light into the optical fiber, whereby the portion of the fluorescence light in the optical fiber is the signal responsive to the fluorescence light. In a particular embodiment, the distal end of the optical fiber is made into an approximately spherical shape.

What is claimed is:

1. A phototherapy method, said method comprising the steps of:
   administering a photosensitive medication to a patient, which medication fluoresces in response to light flux:
      applying energy to a proximal end of a catheter, the distal end of which is adjacent tissue of said patient, to thereby cause light flux from a distal end of said catheter, whereby said light flux causes said photosensitive medication to fluoresce; and
      generating a signal representative of one of said light flux and said fluorescence; and
      coupling said signal by way of said catheter to a location without said patient.

2. A phototherapy method, comprising the steps of:
   administering a photosensitive medication to a patient, which medication fluoresces, at a specific wavelength, in response to light flux:
      applying light flux to a vas of said patient through a catheter, for thereby performing photodynamic therapy, and causing said medication to fluoresce in response to at least the magnitude of said flux; and
      by means of said catheter, routing at least a signal related to said fluorescence to a location without said patient;
      determining, from at least said signal, at least one of (a) the intensity of said flux and (b) the duration of said flux.

3. A method according to claim 2, wherein said step of determining from at least said signal includes the step of determining the power of said fluorescence.

4. A method according to claim 2, wherein said step of administering medication includes one of (a) introducing said medication into said vas directly, (b) introducing said medication orally, and (c) introducing said medication by injection through tissue.

5. A method according to claim 4, wherein said step of administering medication includes the step of administering 5-aminolevulinic acid.

6. A phototherapy method, said method comprising the steps of:
   administering photosensitive 5-aminolevulinic acid medication to a patient, which medication fluoresces at a specific wavelength in response to light flux, said administering being by one of (a) introducing said medication into said vas directly, (b) introducing said medication orally, and (c) introducing said medication by injection through tissue:
      applying light flux to a vas of said patient through a catheter, for thereby performing photodynamic therapy, and causing said medication to fluoresce in response to at least the magnitude of said flux; and
      by means of said catheter, routing at least a signal related to said fluorescence to a location without said patient;
      determining, from at least said signal, at least the power of said fluorescence.
   wherein said step of applying light flux includes the step of applying a light flux having its peak amplitude at a wavelength in the vicinity of 5 ($10^{-7}$) meters.

7. A method according to claim 4, wherein said step of administering medication includes the step of injection of 5-aminolevulinic acid.

8. A method, comprising the steps of:
   administering a photosensitive medication to a patient, which medication fluoresces, at a specific wavelength, in response to light flux, said step of administering medication includes one of (a) introducing said medication into said vas directly, (b) introducing said medication orally, and (c) introducing said medication by injection through tissue:
      applying light flux to a vas of said patient through a catheter, for thereby performing photodynamic therapy, and causing said medication to fluoresce in response to at least the magnitude of said flux; and
      by means of said catheter, routing at least a signal related to said fluorescence to a location without said patient;
      determining, from at least said signal, at least one of (a) the intensity of said flux and (b) the duration of said flux; wherein said step of applying light flux includes the step of:
         generating white light; and
         passing said white light through an optical bandpass filter having a peak in transmission response.

9. A method according to claim 8, wherein said step of passing said white light includes the step of passing said white light through an optical filter having a peak transmission response in the vicinity of 5 ($10^{-7}$) meters.

10. A method according to claim 2, wherein said step of applying light flux includes the step of applying electrical excitation to a plurality of semiconductor light sources located at a distal portion of said catheter, which semiconductor light sources produce light in the vicinity of 630 nm.

11. A phototherapy method, comprising the steps of:
   administering a photosensitive medication to a patient, which medication fluoresces, at a specific wavelength, in response to light flux:
      applying light flux to a vas of said patient through a catheter, for thereby performing photodynamic therapy, and causing said medication to fluoresce in response to at least the magnitude of said flux;
      by means of said catheter, routing at least a signal related to said fluorescence to a location without said patient;
      determining, from at least said signal, at least one of (a) the intensity of said flux and (b) the duration of said flux; and further comprising, before said step of administering medication, the step of sensing the fluorescence of said vas of said patient in response to a flux of light.

12. A method according to claim 2, wherein said step of routing at least a signal related to said fluorescence to a location without said patient includes the step of routing a signal related to said flux to a location without said patient.

13. A catheter for phototherapy, comprising:

an elongated body defining an axis of elongation, a distal region, and a proximal region, said distal region being adapted for introduction into a vas of a patient;

an elongated array of semiconductor light sources associated with said catheter body near said distal region, said semiconductor light sources and said body near said semiconductor light sources being such that, when said semiconductor light sources are energized, light from said semiconductor light sources can radiate away from said body of said catheter;

electrical energization means extending along at least a portion of the length of said body from said proximal region to said array, for energizing at least some of said semiconductor light sources of said array;

a balloon associated with said distal region of said catheter, said balloon having a membrane, said membrane being at least translucent to the light produced by said semiconductor light sources, whereby light radiated away from said semiconductor body in said distal region can pass through said membrane of said balloon;

a balloon inflation lumen extending from said proximal region of said catheter to said balloon;

whereby inflation of said balloon tends to flatten folds in the wall of said vas, and energization of said semiconductor light sources allows light to reach said wall of said vas, and, in the presence of a photosensitive substance in said wall of said vas, said light reaching said wall of said vas results in fluorescence of said photosensitive substance;

said catheter further comprising:
a fluorescence light pickup and transmission arrangement at least partially located in said distal region, for receiving said fluorescence light, and for carrying a signal responsive to said fluorescence light to said proximal region, and for making said signal responsive to said fluorescence light available at said proximal region of said catheter, wherein said fluorescence light pickup and transmission arrangement comprises a photosensor associated with said distal region of said catheter, for receiving said fluorescence light, and for generating an electrical signal in response to said fluorescence light, and for conducting said electrical signal to said proximal end of said catheter.

14. A catheter for phototherapy, said catheter comprising:

an elongated body defining an axis of elongation, a distal region, and a proximal region, said distal region being adapted for introduction into a vas of a patient;

an elongated array of semiconductor light sources associated with said catheter body near said distal region, said semiconductor light sources and said body near said semiconductor light sources being such that, when said semiconductor light sources are energized, light from said semiconductor light sources can radiate away from said body of said catheter;

electrical energization means extending along at least a portion of the length of said body from said proximal region to said array, for energizing at least some of said semiconductor light sources of said array;

a balloon associated with said distal region of said catheter, said balloon having a membrane, said membrane being at least translucent to the light produced by said semiconductor light sources, whereby light radiated away from said semiconductor body in said distal region can pass through said membrane of said balloon;

a balloon inflation lumen extending from said proximal region of said catheter to said balloon;

whereby inflation of said balloon tends to flatten folds in the wall of said vas, and energization of said semiconductor light sources allows light to reach said wall of said vas, and, in the presence of a photosensitive substance in said wall of said vas, said light reaching said wall of said vas results in fluorescence of said photosensitive substance;

said catheter further comprising:
a fluorescence light pickup and transmission arrangement at least partially located in said distal region, for receiving said fluorescence light, and for carrying a signal responsive to said fluorescence light to said proximal region, and for making said signal responsive to said fluorescence light available at said proximal region of said catheter; and an optically dispersive structure lying between said fluorescence light pickup and transmission arrangement and an outer surface of said balloon.

\* \* \* \* \*